(12) United States Patent
Nishimura et al.

(10) Patent No.: US 6,379,318 B1
(45) Date of Patent: Apr. 30, 2002

(54) METHOD FOR PREVENTING BLOOD DENATURATION AND BLOOD TEST TOOL TO BE USED THEREIN

(75) Inventors: Satoshi Nishimura; Kouji Higashino, both of Kyoto (JP)

(73) Assignee: Arkray, Inc., Kyoto (JP)

( * ) Notice: Subject to any disclaimer, the term of this patent is extended or adjusted under 35 U.S.C. 154(b) by 0 days.

(21) Appl. No.: 09/786,147

(22) PCT Filed: Aug. 30, 1999

(86) PCT No.: PCT/JP99/04691

§ 371 Date: May 11, 2001

§ 102(e) Date: May 11, 2001

(87) PCT Pub. No.: WO00/14532

PCT Pub. Date: Mar. 16, 2000

(30) Foreign Application Priority Data

Sep. 2, 1998 (JP) .............................. 10-248653
Jul. 16, 1999 (JP) .............................. 11-203401

(51) Int. Cl.⁷ ................................................ A61B 5/00
(52) U.S. Cl. ..................................................... 600/573
(58) Field of Search ................................ 600/316, 322, 600/573, 584

(56) References Cited

FOREIGN PATENT DOCUMENTS

| JP | 6-34634 | 2/1994 |
|----|---------|--------|
| JP | 7-83920 | 3/1995 |
| JP | 10-17597 | 1/1998 |
| JP | 10-104226 | 4/1998 |

OTHER PUBLICATIONS

Partial Translation of: "Diabetes", 1998, 38: 785–789.
International Search Report for PCT/JP99/04691, dated Jan. 18, 2000.

Primary Examiner—Max Hindenburg
(74) Attorney, Agent, or Firm—Merchant & Gould, P.C.

(57) ABSTRACT

A blood test tool with which blood in a dried state can be held without denaturation. In the blood test tool wherein a card made of filter paper is impregnated with the blood and then the blood is held in a dried state, a carboxylic acid such as citric acid is added to the part for holding blood. Thus, the carboxylic acid exerts an effect of preventing the blood in the dried state from denaturation. It is preferable to add a non-reducing sugar (sucrose, etc.), an anticoagulant (EDTA, etc.) and an antioxidant (glutathione, etc.) together with the carboxylic acid. This blood test tool can be produced by impregnating a filter paper card with a solution containing citric acid, etc. dissolved therein and then air-drying.

21 Claims, 11 Drawing Sheets

Blood Collection Card

| Collection date | Year | Month | Day |
|---|---|---|---|
| Name | | Sex | M   F |
| Date of birth | Year | Month | Day |

Smear the circles with collected blood

Blood Collection Card

| Collection date | Year | Month | Day | | |
|---|---|---|---|---|---|
| Name | | | | Sex | M  F |
| Date of birth | Year | Month | Day | | |

Smear the circles with collected blood

METHOD FOR PREVENTING BLOOD DENATURATION AND BLOOD TEST TOOL TO BE USED THEREIN

TECHNICAL FIELD

The present invention relates to a method for preventing the denaturation of blood, particularly hemoglobin, and a blood test tool to be used therein.

BACKGROUND ART

Hemoglobin A1c (HbA1c) in which hemoglobin (Hb) is bonded to glucose reflects the average glucose level of the body one or two months earlier. Therefore, it is widely used in physical examinations for geriatric diseases or treatment and consultation therefor. However, since it takes a long time to measure HbA1c, for example, even if the blood is collected from outpatients when they visits to hospital, the result of the examination of HbA1c is generally evaluated when the patient visits to the hospital the next time. Therefore, although the measurement value of HbA1c is an important factor for diagnosis of diabetes, actually, it has not been used effectively for treatment.

To solve this problem, a blood collection card made of filter paper has been proposed ("Diabetes" Vol. 38, No. 10 (1995), JP10-104226A, etc.). The patients collect blood onto the collection card by themselves and allow the collection card to be impregnated with the collected blood, dried, and then mail the card to the hospital. In the hospital where this card is received, the part impregnated with the blood of the card is cut out or punched out (punch-out), and then blood is eluted therefrom. The eluted blood is examined for the predetermined items including HbA1c, etc. When the patient visits to the hospital, the treatment or diagnosis is performed based on the examination results.

However, one to several days are required for collecting blood onto the collection card, mailing the collection card, and examining the blood. Furthermore, since the blood is held in a dried state in this case, Hb may be denatured. For example, if Hb and glucose react with each other in the blood collection card, and HbA1c is newly produced, the value of HbA1c produced in the body cannot be determined exactly. Furthermore, if the protein-denaturation of Hb occurs, a denatured Hb peak appears in the measurement using the high performance liquid chromatography (HPLC), and a denatured Hb peak appears and affects the peak of HbA1c, which may lead to the inability to measure or measurement errors.

DISCLOSURE OF INVENTION

It is therefore an object of the preset invention to provide a method for preventing the denaturation of blood in a dried state and the blood test tool for using the method.

In order to attain the above-mentioned object, the present invention provides a method for preventing the denaturation of blood in a dried state, wherein the blood in a dried state and a carboxylic acid are allowed to be present together When carboxylic acid and blood are allowed to be present together, even in a dried state, the production of new HbA1c is prevented and also the protein-denaturation of Hb is prevented. In the production of HbA1c, first Hb and glucose are reacted nonenzymatically with each other (a reversible reaction) to produce an unstable aldoimine, which is formed into a stable ketoamine (HbA1c) through an Amadori rearrangement. Carboxylic acid is believed to prevent the production of the unstable aldoimine so as to prevent the production of new HbA1c. On the other hand, a mechanism of preventing the protein-denaturation of Hb is not clear. However, as known from the below mentioned Examples, the effect is significant.

Furthermore, in the present invention, "Hb is denatured" means not only that the structure of the protein is changed like protein-denaturation, but also modification of Hb by other materials, and the like.

It is preferable in the method for preventing the denaturation of blood of the present invention that carboxylic acid is added to blood in a non-dry state and then the blood is dried. In this way, if carboxylic acid is added to a liquid blood before being dried, since the blood and carboxylic acid can be brought into contact with each other sufficiently, it is possible further to prevent the denaturation of the blood in the following dried state.

It is preferable in the present invention that the carboxylic acid is citric acid because it exhibits a high effect in preventing the denaturation of Hb. However, in the present invention, as the carboxylic acid, for example, oxalic acid, pyruvic acid, acetic acid, etc. may be used. The amount of carboxylic acid to be added is generally 1.5 to 10 parts by weight, and preferably 2.5 to 6 parts by weight, with respect to 100 parts by weight of the blood in a non-dry state.

It is preferable in the method for preventing the blood denaturation of the present invention that in addition to carboxylic acid, a non-reducing sugar and the blood are allowed to be present together because the non-reducing sugar is not likely to be reacted with Hb and can prevent the denaturation of Hb further. It is preferable that the non-reducing sugar is sucrose. Besides, a non-reducing sugar such as trehalose can be used. The amount of the non-reducing sugar is generally 10 to 50 parts by weight, and preferably 20 to 30 parts by weight, with respect to 100 parts by weight of the blood in a non-dry state.

It is preferable in the method for preventing the blood denaturation of the present invention that, in addition to the carboxylic acid and the non-reducing sugar, at least one of an anticoagulant and an antioxidant is allowed to be present together with blood. An example of the anticoagulant includes ethylenediaminetetraacetic acid (EDTA), heparin, oxalic acid salt, and the like. Among them, EDTA is preferable. The amount of the anticoagulant is generally 1 to 5 parts by weight, and preferably 1.5 to 3 parts by weight, with respect to 100 parts by weight of the blood in a non-dry state. An example of the antioxidant includes glutathione (GSH), α-tocopherol, and the like. Among them, GSH is preferable. The amount of the antioxidant is generally 0.1 to 8 parts by weight, and preferably 0.1 to 3 parts by weight, with respect to 100 parts by weight of the blood in a non-dry state.

It is preferable in the method for preventing the blood denaturation of the present invention that the blood is in a dried state, with a porous material being impregnated with the blood and the blood dried.

Next, according to the blood test tool of the present invention, the blood test tool holds blood in a dried state with a porous material impregnated with the blood, and a part for holding the blood of the porous material (hereinafter, "blood holding part" will be referred to) contains carboxylic acid.

In the blood test tool of the present invention, like in the method for storing the blood of the present invention, it is preferable that the carboxylic acid is citric acid. The above-mentioned carboxylic acids may be used. Furthermore, the amount of carboxylic acid is the same as in the above.

It is preferable in the blood test tool of the present invention that the blood holding part contains a non-reducing sugar, in addition to carboxylic acid. The non-reducing sugar is preferably sucrose, and the above-mentioned non-reducing sugar can also be used. Furthermore, the amount of the non-reducing sugar is the same as in the above.

It is preferable in the blood test tool of the present invention that the blood holding part contains at least one of an anticoagulant and an antioxidant in addition to carboxylic acid and non-reducing sugar. The anticoagulant is preferably EDTA, and the above-mentioned anticoagulants also can be used. Furthermore, the amount of the anticoagulant is the same as in the above. The above-mentioned antioxidant is preferably GSH, and the above-mentioned antioxidants also can be used. The amount of the antioxidant is the same as in the above.

It is preferable in the blood test tool of the present invention that the blood holding part is surrounded by a blood anti-diffusion layer provided in or around the porous material.

When the blood test tool of the present invention has such a liquid anti-diffusion layer, it is possible to prevent the blood smeared on the porous material from diffusing, so that the diffusion of the blood in the direction of thickness is promoted. Therefore, the blood can be secured in a constant region (the blood holding part) of the porous material. Furthermore, since the blood holding part is the above-mentioned constant region, it is possible to prevent a sieve effect by the porous material. For example, there is little concentration difference in the components such as the hemocytes between the central part to which the blood is smeared and the diffusion part in which the blood is diffused in the planar direction. Thus, it is possible to maintain homogeneously the concentration of the components in blood in the planar direction of the blood holding part. Therefore, for example, the part to be punched out for the blood holding part is not particularly limited, so that the procedure is much simplified, and also measurement can be carried out with excellent repeatability.

It is preferable in the blood test tool of the present invention that the blood anti-diffusion layer has a non-porous structure since it is possible reliably to prevent the blood in the blood holding part from diffusing to the outside.

The layer of the non-porous structure may be formed, for example, by impregnating the porous material with resin so as to make the porous structure into a non-porous structure. An example of the resin with which the porous material is impregnated includes, for example, polyvinyl butyral, ethyl cellulose, cellulose acetate, polyethylene terephthalate, polyethylene, gelatin, and the like.

Furthermore, the liquid anti-diffusion layer may be a member, for example, a plastic such as polystyrene, polyethylene terephthalate, polyvinyl chloride, etc.; glass; metal; and the like. The porous material may be surrounded by these members.

Furthermore, it is preferable that the blood anti-diffusion layer is hydrophobic since it is possible to prevent the blood from diffusing regardless of a non-porous structure and a porous structure. An example of the hydrophobic blood anti-diffusion layer may be a layer formed by impregnating the porous material with hydrophobic resin. An example of the usable hydrophobic resin includes, for example, polyacetal resin, fluororesin, silicone resin, and the like.

It is preferable in the blood test tool of the present invention that the porous material is a card type. The card type blood test tool is excellent in handling property and is convenient when mailed, and the like.

It is preferable in the blood test tool of the present invention that the blood holding part is supported by a supporter and is detachable from the supporter. In this way, if the blood holding part is detachable from the supporter, for example, a step of punching out the card can be omitted and the generation of pieces can be prevented. Therefore, prior to the measurement, it is not necessary to remove pieces by filtration or centrifuge, thus making the measurement more easily.

It is preferable that the blood test tool of the present invention has a cylindrical shape with a bottom and the bottom part is formed of a porous material. When a test tool has such a cylindrical shape with a bottom, the blood test tool itself can be used as a container for elution, and thus it is not necessary to prepare the particular container for elution. Furthermore, for example, after the porous material of the blood test tool is impregnated with blood and the blood is dried, the eluate (extractant) is put into the test tool so as to infiltrate into and permeate the porous material at the bottom part, thereby eluting the blood. Thus, it is possible to elute the blood easily and promptly. Specifically, for example, when the eluate that is put into the cylindrical blood test tool with a bottom infiltrates into the porous material by gravitaty, and when the eluate passes through the porous material, the blood held is eluted (extracted). The eluate passing through the porous material is collected in the container located in the lower part of the blood test tool, whereby the elution is completed. With such a blood test tool, for example, right after the elution is completed, the measurement can be performed, so that the punching-out step can be omitted, and the generation of small pieces of the porous material is prevented. Furthermore, a special machine such as a shaker, etc. is not used and the elution can be performed briefly for a short time.

BRIEF DESCRIPTION OF DRAWINGS

FIGS. 3(a) and 3(b) are plan views showing a blood test tool of a further embodiment according to the present invention; wherein FIG. 3(a) shows a blood holding part surrounded by a liquid anti-diffusion layer; and FIG. 3(b) shows a holder supporting the blood holding part.

FIGS. 5(a) and 5(b) are plan views showing a blood test tool of still another embodiment according to the present invention; wherein FIG. 5(a) shows a blood holding part surrounded by a liquid anti-diffusion layer; and FIG. 5(b) shows a holder supporting the blood holding part.

BEST MODE FOR CARRYING OUT THE INVENTION

The blood test tool of the present invention can be manufactured by, for example, impregnating a porous material with a solution in which carboxylic acid (if necessary, a non-reducing sugar, an anticoagulant and an antioxidant) is dissolved or diffused, and then by drying the impregnated solution. The drying method may be natural drying or air-drying. The average pore diameter of the porous layer is not particularly limited as long as it is sufficient to allow the blood to infiltrate and to be held, but generally the pore diameter is in the range from 3 to 10 $\mu$m.

The porous material is not particularly limited. However, filter paper, glass filter, resin porous film, and the like generally are used. Among them, filter paper is preferable from the viewpoint of the cost or handling etc. Furthermore, an example of the material of the resin porous film includes polystyrene, polyester, nylon, cellulose nitrate, polycarbonate, and the like.

(Embodiment 1)

Figure 1:
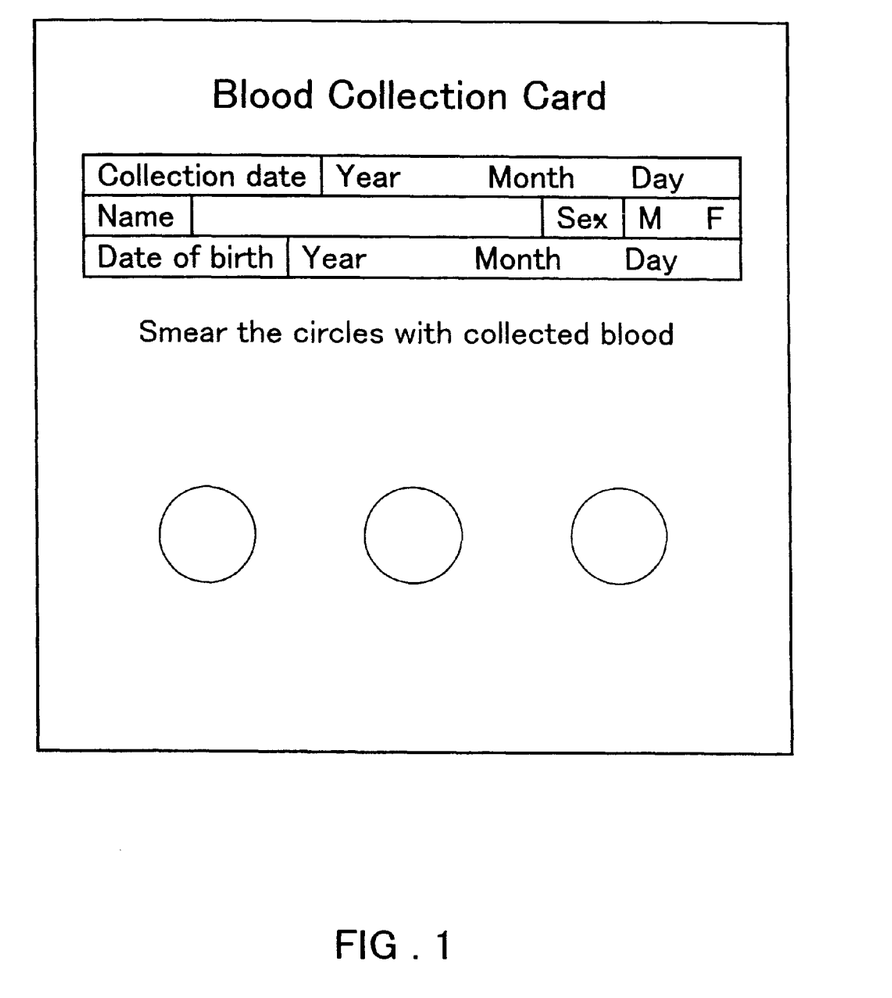
FIG. 1 is a plan view showing a blood test tool in one embodiment according to the present invention.

FIG. 1 shows one example of the blood test tool according to the present invention. As shown in FIG. 1, this blood test tool is a card type. On the lower part of this card, there are three parts onto which blood is smeared (i.e. blood holding parts) shown by circles, and on the upper part of the card predetermined matters such as name can be written. The entire part of this blood test tool may be formed of a porous material such as filter paper etc., or only the blood holding part may be formed of a porous material. This blood holding part includes carboxylic acid, and if necessary, a non-reducing sugar, an anticoagulant and an antioxidant. The size of this blood test tool is not particularly limited, but is preferably a post card size or a little bit smaller than the post card size from the viewpoint of the convenience in mailing, etc. Furthermore, in order to shield the blood holding parts from the outer environment, the surface of the blood holding parts may be shielded by a resin film, etc. after the part is impregnated with blood.

Subjects etc. collect the blood from the finger tip etc. by themselves and smear the holding part shown by circles of the blood test tool with the collected blood. Thus, the smeared blood rapidly infiltrates and is held therein. Then, the patient allows the smeared blood to dry by natural drying, air-drying, or the like, puts it into envelope, etc., and mails it to the predetermined hospital or examination institution. Between the time the blood sample is mailed and the time the blood is examined, the denaturation of Hb is prevented by action of the carboxylic acid. Thus, the blood holding part of the blood test tool is cut out or punched out in the hospital etc., and then the eluting procedure is carried out and the resultant eluate is examined with respect to the predetermined items, for HbA1c, etc.

(Embodiment 2)

Figure 2:
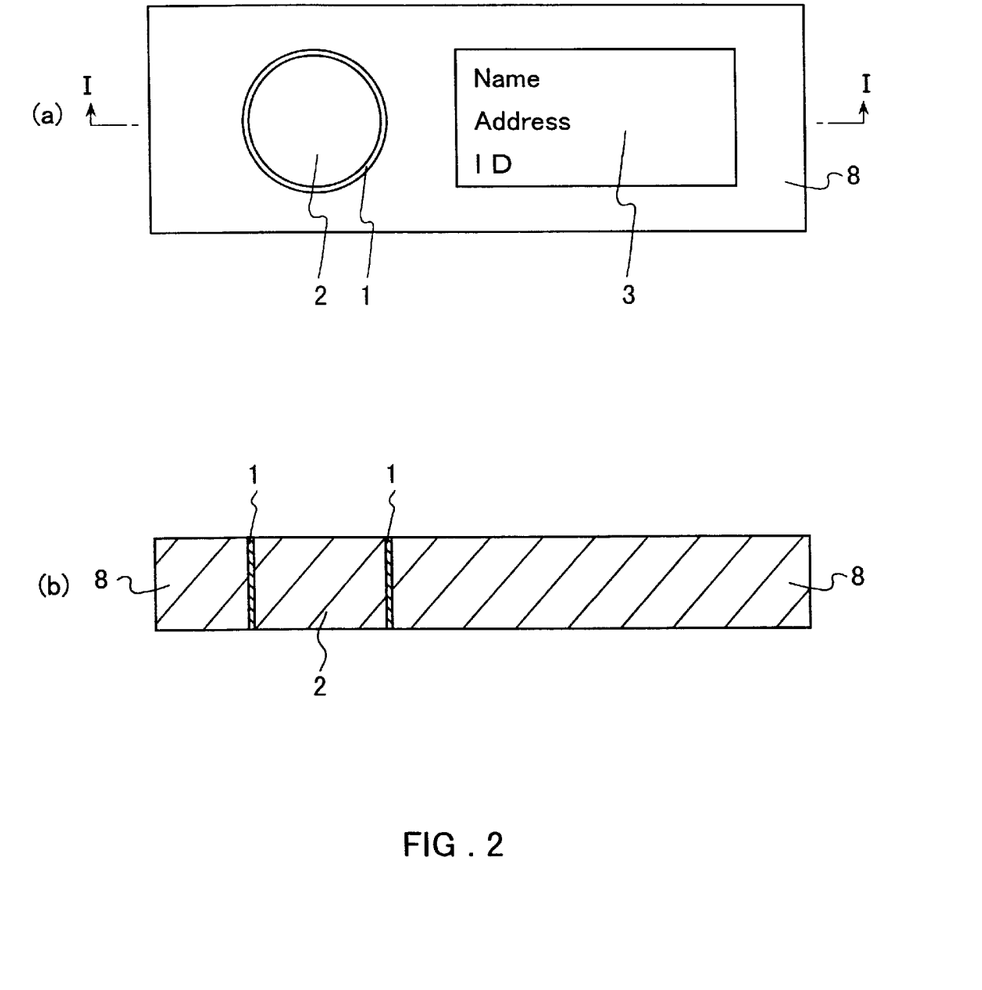
FIG. 2(a) is a plan view showing a blood test tool of another embodiment according to the present invention.
FIG. 2(b) is a sectional view thereof.

FIG. 2 shows an example of the blood test tool having a liquid anti-diffusion layer according to the present invention. FIG. 2(a) is a top view showing the schematic structure of the blood test tool; and FIG. 2(b) is a sectional view in the I—I direction of the blood test tool. As shown in FIG. 2, the entire part of this blood test tool is formed of rectangular flat porous material 8 and includes a ring-shaped liquid anti-diffusion layer 1 therein, and the part surrounded by the ring-shaped liquid anti-fusion layer 1 is a blood holding part 2. Furthermore, a part of the surface of the porous material 8 constitutes a part to be written 3 where name, address, ID number, etc. are written.

The size of this blood test tool has, for example, maximum length of 40 to 150 mm; maximum width of 10 to 100 mm; and the maximum thickness of 5 to 100 $\mu$m.

The size and shape of the blood holding part 2 are not particularly limited, but when the shape is a circle, the diameter is, for example, 5 to 50 mm. Furthermore, similar to the above, carboxylic acid, and if necessary, a non-reducing sugar, an anticoagulant and an antioxidant, are present in the blood holding part 2. Furthermore, the shape or width of the liquid anti-diffusion layer 1 also is not particularly limited, but the width is, for example, 0.5 to 5 mm.

In the blood test tool, as mentioned above, the whole structure may be formed of a porous material, or only the blood holding part 2 may be formed of a porous material. As the porous material, for example, a filter paper, glass filter, a resin porous film, and the like can be used, and among them, the filter paper is preferably used from the viewpoint of the cost or handling, etc. The average pore diameter of the porous material is not limited as long as the blood can infiltrate and be held, but the hole diameter is, for example, 1 to 10 $\mu$m.

The liquid anti-diffusion layer 1 can be formed by, for example, preparing a solution in which the above-mentioned resin is dissolved or diffused in the solvent (hereinafter, "resin solution" will be referred to), and by printing or applying the resin solution onto the porous material 8. The size of the blood holding part 2 can be determined appropriately by the formation of this liquid anti-diffusion layer 1. In the thus formed liquid anti-diffusion layer 1, the porous structure of the porous material may be made into a non-porous structure by the resin, or it may have a porous structure if it is made to be hydrophobic by impregnating the porous material with hydrophobic resin.

In this blood test tool, for example, when the blood is smeared onto the surface of the blood holding part 2, the blood diffuses and infiltrates in the face direction and the thickness direction of the blood holding part 2. At this time, with the liquid anti-diffusion layer 1, it is possible to prevent blood from diffusing toward the porous material 8 outside of the blood holding part 2.

(Embodiment 3)

Figure 3:
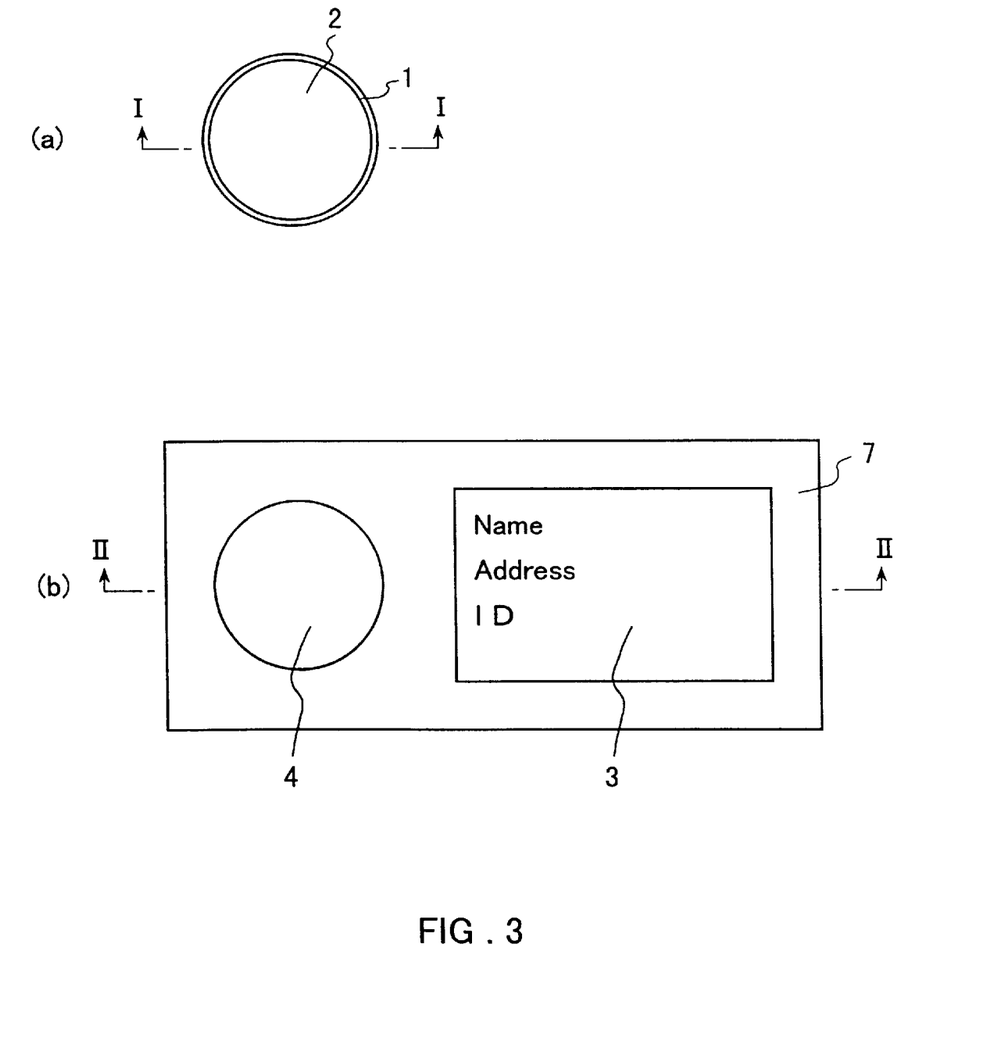
Figure 4:
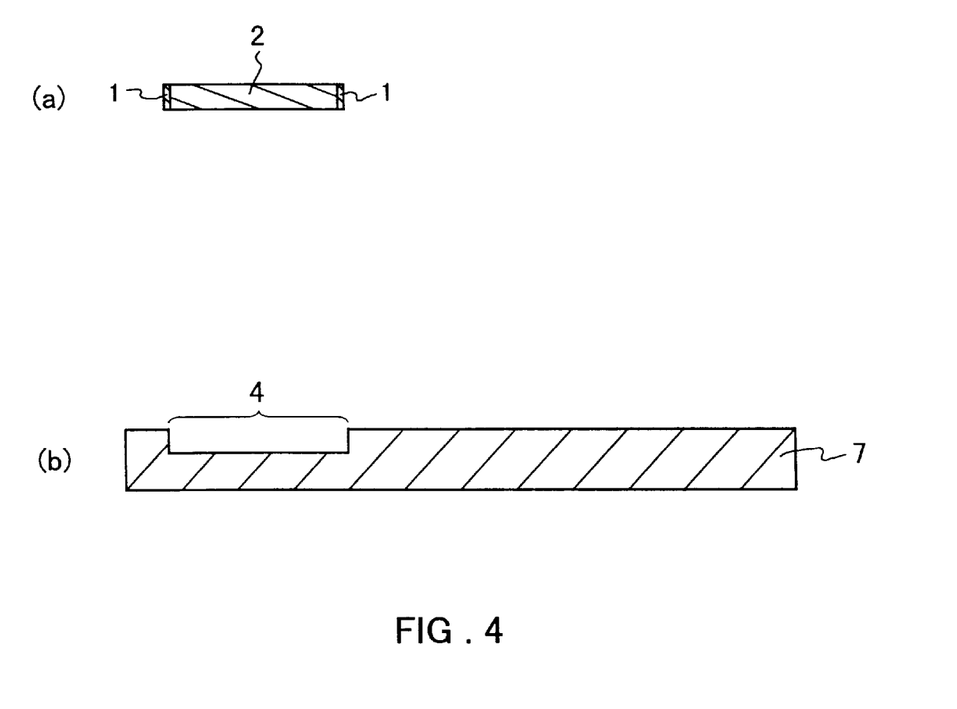
FIG. 4(a) is a sectional view showing the blood holding part of the above-mentioned embodiment.
FIG. 4(b) is a sectional view showing the holder.

FIGS. 3 and 4 show an example of the blood test tool including a detachable blood holding part according to the present invention. FIG. 3(a) is a top view showing a blood holding part surrounded by a liquid anti-diffusion layer; and FIG. 3(b) is a top view showing a holder supporting the blood holding part. Furthermore, FIG. 4(a) is a sectional view in the I—I direction of the blood holding part surrounded by the liquid anti-diffusion layer shown in FIG. 3;

and FIG. 4(b) is a sectional view in the II—II direction of the holder shown in FIG. 3. Moreover, in FIGS. 3 and 4, the same parts as in FIG. 2 are given the same remarks.

Such a blood test tool can be used by, for example, fitting the blood holding part 2 surrounded by the liquid anti-diffusion layer 1 shown in FIGS. 3(a) and 4(a) into a concave supporting portion 4 of the holders 7 shown in FIGS. 3(b) and 4(b). Moreover, the both may be adhered detachably by adhesives, etc.

The blood holding part 2 surrounded by the liquid anti-diffusion layer 1 shown in FIGS. 3(a) and 4(a), can be formed by, for example, punching out the porous material in the form of circle, and then applying the resin solution, etc. on the side face of the circle punched material. Similar to the above, this blood holding part 2 includes carboxylic acid, and if necessary, a non-reducing sugar, an anticoagulant and an antioxidant.

When the blood is eluted by using the blood test tool in which the blood holding part 2 is detachable, for example, the blood holding part 2 surrounded by the liquid anti-diffusion layer 1 is detached from the holder 7 and immersed in the eluate. Since, for example, the above-mentioned resin, etc. is applied around the blood holding part 2, the porous materials is prevented from getting loose and being released into the eluate. Therefore, prior to the measurement, it is not necessary to remove pieces by filtration or centrifuge. Moreover, the shape, etc. of the blood holding part and liquid anti-diffusion layer is not particularly limited.

(Embodiment 4)

Figure 5:
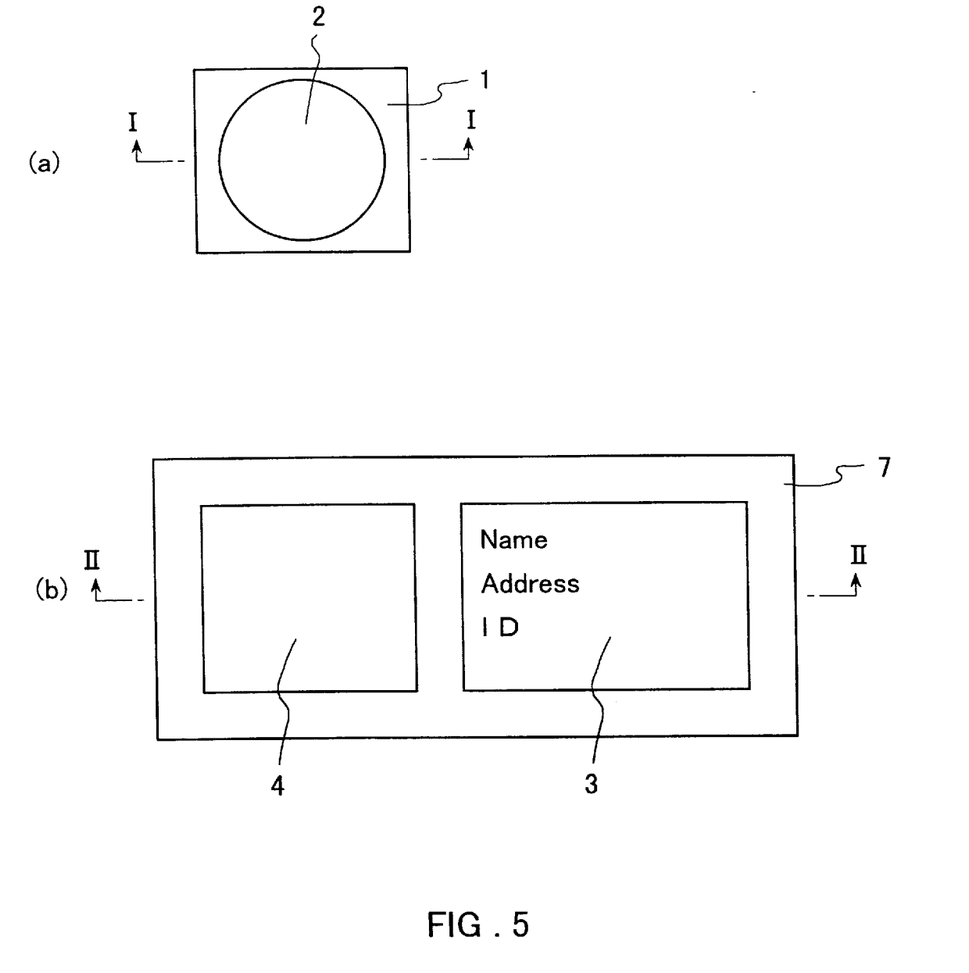

FIG. 5 shows an example of the blood test tool according to the present invention having a different shape for the liquid anti-diffusion layer. FIG. 5(a) is a top view showing a blood holding part surrounded by a liquid anti-diffusion layer; and FIG. 5(b) is a top view showing a holder supporting the blood holding part. In FIG. 5, the same parts as in FIG. 3 are given the same remarks. As shown in this figure, the external shape of the liquid anti-diffusion layer 1 is a square, and a circular blood holding part 2 is formed therein.

The liquid anti-diffusion layer 1 and the blood holding part 2 can be formed by impregnating the circumference of the circle part of the porous material with the resin solution by printing or applying, and by punching out the porous material in a square form.

Moreover, in the blood test tool of this Example, the other structure, and using method are the same as in the proceeding examples.

(Embodiment 5)

Figure 6:
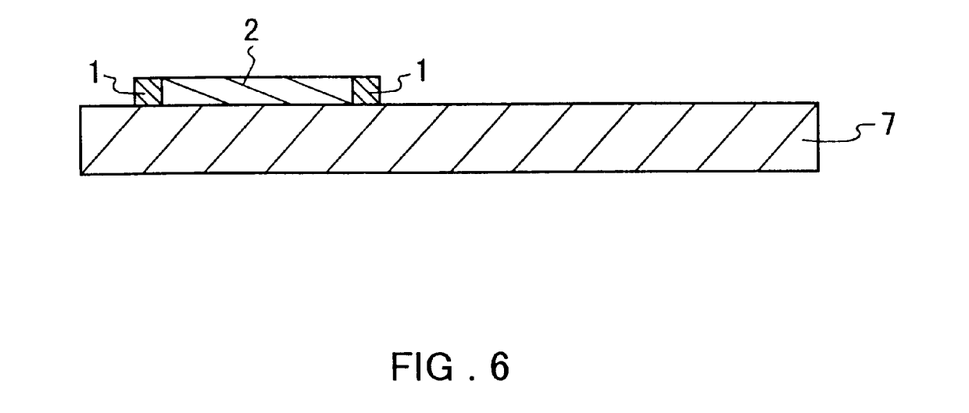
FIG. 6 is a sectional view showing a blood test tool of yet another embodiment according to the present invention.

FIG. 6 is a sectional view showing another example of the blood test tool including a detachable blood holding part surrounded by the anti-diffusion layer according to the present invention. As shown in FIG. 6, in this blood test tool, a blood holding part 2 surrounded by the liquid anti-diffusion layer 1 is laminated on a flat holder 7. Furthermore, in order to prevent the blood holding part 2 from peeling off from the holder 7, the blood holding part 2 and the holder 7 are adhered detachably by the adhesives.

Moreover, in the blood holding part of the blood test tool of this embodiment, the structure and the using method are the same as in the proceeding embodiments.

(Embodiment 6)

Figure 7:
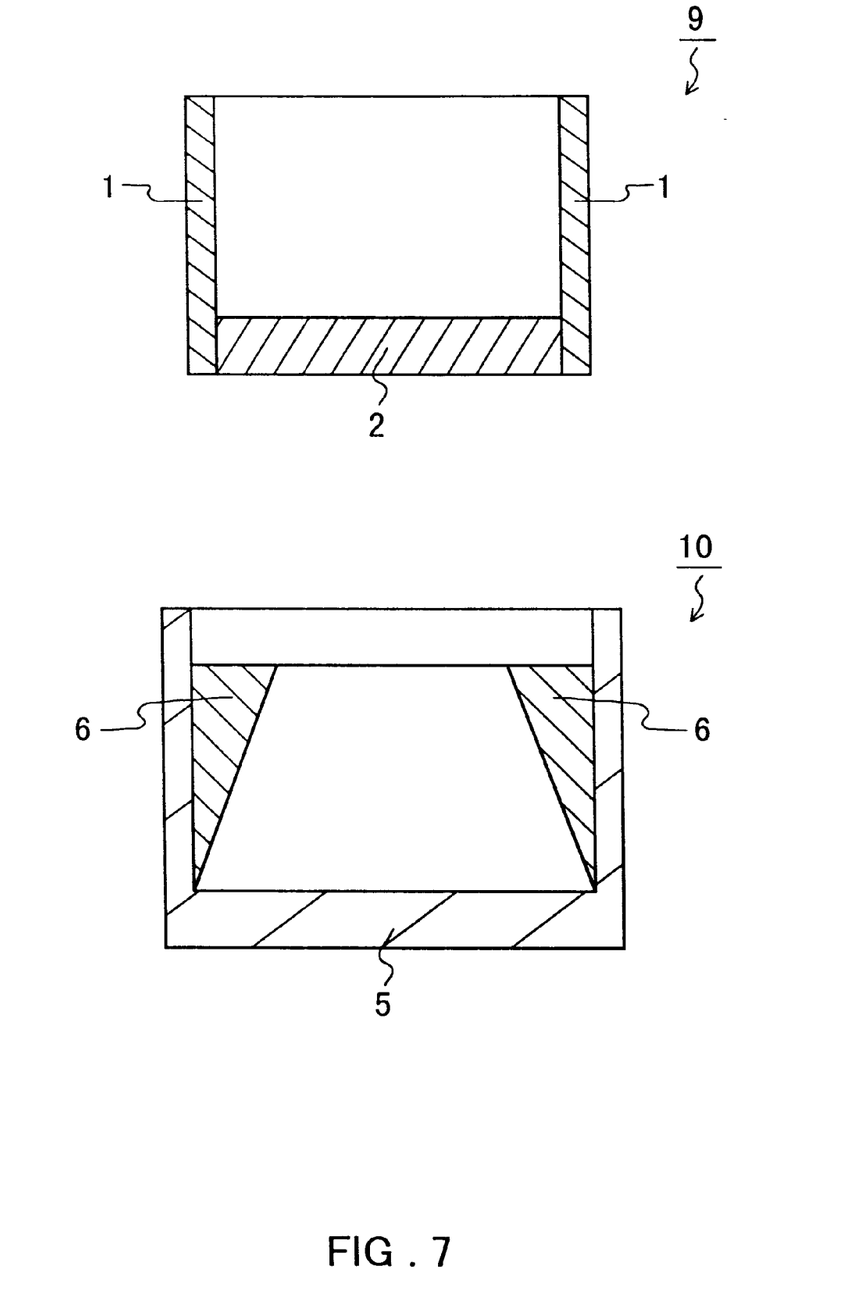
FIG. 7 is a sectional view showing a blood test tool of a further embodiment according to the present invention; and a sectional view showing an example of an eluate collection vessel to be used for collecting blood held in the blood test tool.

Next, FIG. 7 is a sectional view showing one example of a cylindrical blood test tool with a bottom according to the present invention. In FIG. 7, reference numeral 9 denotes a cylindrical blood test tool with a bottom, and 10 denotes an eluate collection vessel. As shown in figure, this cylindrical blood test tool with a bottom 9 is formed by fitting the porous material into the bottom part of the cylindrical body. The cylindrical body is a blood anti-diffusion layer 1 and the porous material is a blood holding part 2. Furthermore, the eluate collection vessel 10 is provided with a holding part 6 for holding the blood test tool 9 on the internal wall of the container 5. Moreover, in FIG. 7, the same parts as in FIG. 2 are given the same remarks.

The shape of the cylindrical body (the liquid anti-diffusion layer 1) is not particularly limited. An example of the shapes includes cylindrical shape, hollow prismatic shape, or the like.

Such a cylindrical blood test tool with a bottom 9 can be formed by, for example, punching out the porous material so that the punched-out part becomes the bottom part of the cylindrical body and then by fitting it into the cylindrical body. At this time, preferably the contact faces of both parts are adhered by adhesives, etc. Similar to the above, this blood holding part 2 (porous material of the bottom part) includes carboxylic acid, and if necessary, a non-reducing sugar, an anticoagulant and an antioxidant.

The cylindrical blood test tool with a bottom 9 has, for example, an internal depth of 5 to 50 mm, and a volume of 1 to 3 ml. Furthermore, it is preferable that the inner diameter of the eluate collection vessel 10 is larger than the outer diameter of the cylindrical blood test tool with a bottom 9. For example, the eluate collection vessel 10 has an inner diameter of 7 to 55 mm, an internal depth of 5 to 50 mm, and a volume of 1 to 5 ml. It is preferable that the cylindrical blood test tool with a bottom 9 and the eluate collection vessel 10 are detachable from each other. The shape of the holder 6 is not particularly limited as long as the holder 6 can hold the cylindrical blood test tool with a bottom 9. However, the shape having a tapered surface as shown in this figure is preferred because it can collect an eluate containing blood along the tapered face.

Material of the cylindrical body (liquid anti-diffusion layer) 1 of the cylindrical blood test tool with a bottom 9 and a container 5 of the eluate collection vessel 10 are not particularly limited. For example, plastic, glass, metal, and the like, can be used and a transparent member is preferable because the amount of added eluate and the amount of the collected eluate can be checked from the outside. An example of the useful material includes a plastic such as polystyrene, polyethylene terephthalate, etc. Furthermore, a material of the holder 6 is not particularly limited, and an example of the material includes a plastic such as polystyrene, polyethylene terephthalate, and the like.

Figure 8:
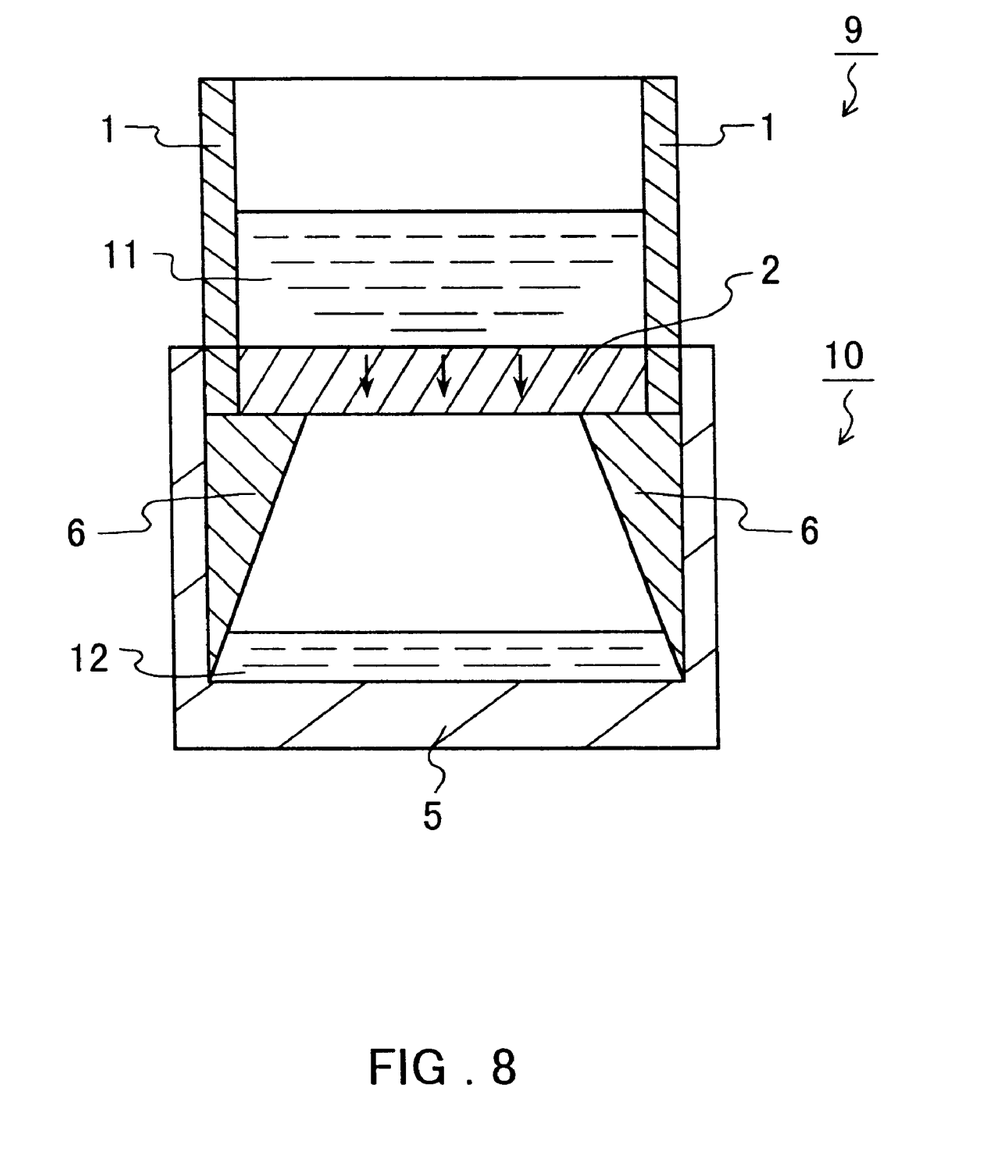
FIG. 8 is a sectional view showing a state in which the blood test tool and the eluate collection vessel are being used when the blood held in the blood test tool is collected in the above-mentioned embodiment.

An example of the method for collecting blood by using such a cylindrical blood test tool with a bottom 9 is explained with reference to the sectional view of FIG. 8. In FIG. 8, the same parts as in FIG. 7 are given the same remarks.

For example, first, the bottom part (a blood holding part 2) of the cylindrical blood test tool with a bottom 9 is smeared with the blood and dried. Then, as shown in this figure, this cylindrical blood test tool 9 is placed on the holder 6 of the eluate collection vessel 10. Then, an eluate 11 is put into the sample holding tool 9. The eluate 11 moves in the blood holding part 2 in the thickness direction (the direction shown by an arrow in FIG. 8) by the natural drop with infiltrating, and elutes the held blood and permeates the blood holding part 2. The eluate 12 containing the permeated blood moves along the holder 6 provided on the eluate collection vessel 10 and is stored in the eluate collection vessel 10. Moreover, when the blood is eluted, for example, the eluate 11 is forced to infiltrate and permeate the porous material (the blood holding part) 2 by setting the internal pressure of the cylindrical blood test tool with a bottom 9 to be positive.

(Embodiment 7)

The following is an explanation of Examples in which the prevention of the blood denaturation in a dried state is actually confirmed by using the blood test tool of the present invention and Comparative Example.

EXAMPLE 7-1

Comparative Example 1

Monohydrate of citric acid was dissolved in pure water in the amounts of 20 mg/ml and 50 mg/ml to prepare two kinds of treating solutions. Two kinds of blood test tools (a and b) were formed by impregnating the circular filter paper (ADVANTEC 101, diameter 100mm, product of TOYO ROSHI) with 2.5 ml of the treating solution and then air-drying. 20 mg/ml treating solution was used for the blood test tool a; and 50 mg/ml treating solution was used for the blood test tool b. Furthermore, Comparative Example 1 used a blood test tool c, in which filter paper was not treated with citric acid aqueous solution.

The three kinds of blood test tools (a, b, and c) were impregnated with fresh blood collected from normal subjects and then air-dried. Then, the three kinds of blood test tools (a, b, and c) were stored at room temperature for 0, 2, 7, 8, and 10 days, and then the part that was impregnated with the blood was punched out in a shape of circle with a diameter of about 6 mm by using a punch. This punched part was put into 0.6 ml of eluate (High-Auto A1C specific diluent, product of KYOTO DAIICHI KAGAKU CO. LTD) and was allowed to stand still for about 10 minutes, and the eluting procedure was performed. The HbAlc in this eluate was measured by the use of an automatic glycohemoglobin measuring device (High-Auto A1C HA-8150, KYOTO DAIICHI KAGAKU CO. LTD) in a hemolytic mode. Furthermore, as a control, HbAlc in the blood right after collection from healthy subjects was measured by using the automatic glycohemoglobin measurement device. Table 1 shows the results. Moreover, in Table 1, the amount of HbAlc in blood is expressed by percentage (%) with respect to the whole amount of Hb. The same is true in the following tables.

TABLE 1

| Blood test | Amount of HbAlc in blood (%) | | | | |
|---|---|---|---|---|---|
| | Days stored (days) | | | | |
| tool | 0 | 2 | 4 | 7 | 10 |
| a | 4.97 | 5.32 | 5.30 | 5.58 | 5.88 |
| b | 4.74 | 4.84 | 4.88 | 4.86 | 4.99 |
| c | 5.78 | n.m | n.m | n.m | n.m |
| Control | 5.03 | — | — | — | — | n.m = not measurable

As is apparent from Table 1, the blood test tools a and b, which had been treated with citric acid aqueous solutions, were able to prevent the production of HbAlc. On the contrary, with the blood test tool c, which had not been treated with a citric acid aqueous solution, HbAlc and denatured hemoglobin were increased as the storing time passes, thus to make it impossible to perform measurement.

EXAMPLE 7-2

Comparative Example 2

As shown in Table 2, monohydrate of citric acid, EDTA·2Na, sucrose and reduced glutathione were dissolved in pure water so as to prepare five kinds of treatment solutions (d, e, f, g and h).

TABLE 2

| | Treating solution (mg/ml) | | | | |
|---|---|---|---|---|---|
| | d | e | f | g | h |
| Monohydrate of citric acid | 30 | 30 | 50 | 50 | 0 |
| EDTA·2Na | 17 | 17 | 17 | 17 | 0 |
| Sucrose | 300 | 300 | 300 | 600 | 0 |
| Reduced glutathione | 1 | 0 | 1 | 1 | 0 |

Five blood test tools (d, e, f, g, and h) were formed by impregnating the circular filter paper with the five treatment solutions and then air-drying. Moreover, remarks given to the blood test tools (d, e, f, g, and h) correspond to the remarks of the treatment solutions (d, e, f, g, and h). Furthermore, the blood test tool h was used in Comparative Example 2.

The five blood test tools were impregnated with fresh blood collected in the presence of heparin from healthy subjects and air-dried. Then, the five blood test tools (d, e, f, g, and h) were stored at room temperature for 0, 1, 3 and 6 days, and then the part that is impregnated with the blood was punched out by a punch so as to form a circle shape with a diameter of about 6 mm. The punched-out part was put into 0.6 ml of eluate and allowed to stand still for about 10 minutes and the eluting procedure was performed. The HbAlc in the eluate was measured by the use of an automatic glycohemoglobin measuring device to measure the eluate in a hemolytic mode. Furthermore, as a control, HbAlc of the blood collected in the presence of heparin from healthy subjects was stored similarly and was measured by the use of the automatic glycohemoglobin measurement device. Table 3 shows these results.

TABLE 3

| Blood test | Amount of HbAlc (%) | | | |
|---|---|---|---|---|
| | Days stored (days) | | | |
| tool | 0 | 1 | 3 | 6 |
| d | 5.27 | 4.85 | 4.75 | 4.77 |
| e | 5.19 | 4.85 | 4.77 | 4.81 |
| f | 5.16 | 4.96 | 4.97 | 4.98 |
| g | 5.24 | 5.00 | 5.05 | 5.05 |
| h | 5.91 | 6.70 | 7.10 | n.m |
| control | 5.31 | 5.33 | 5.33 | 5.26 | n.m = not measurable

As is apparent from Table 3, in the blood test tools (d, e, f, and g) using sucrose, EDTA and glutathione in addition to citric acid, the production of HbAlc was able to be prevented. On the other hand, in the blood test tool h (Comparative Example 2), it was confirmed that the HbAlc was significantly increased.

EXAMPLE 7-3

Figure 9:
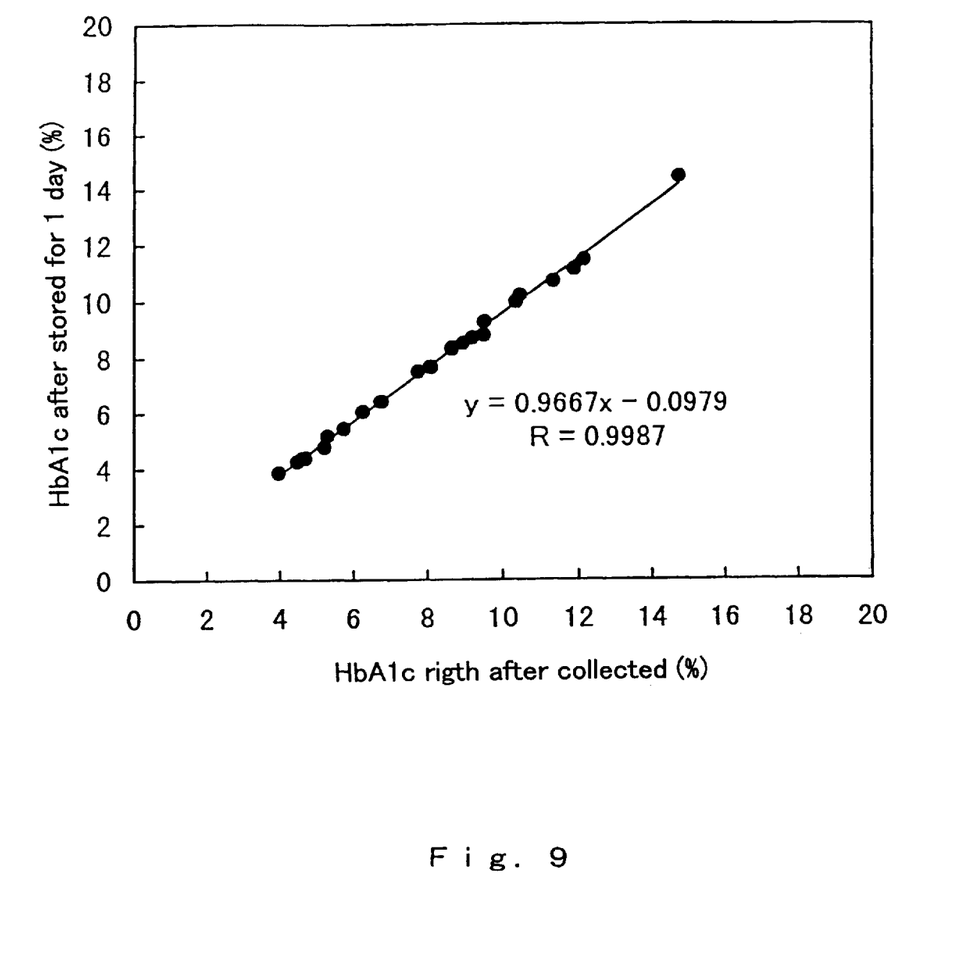
FIG. 9 is a graph showing the correlation between HbA1c stored for one day after the blood sample is collected by using a blood collection tube and HbA1c right after the blood sample is collected by using a blood collection tube in a further embodiment according to the present invention.
Figure 10:
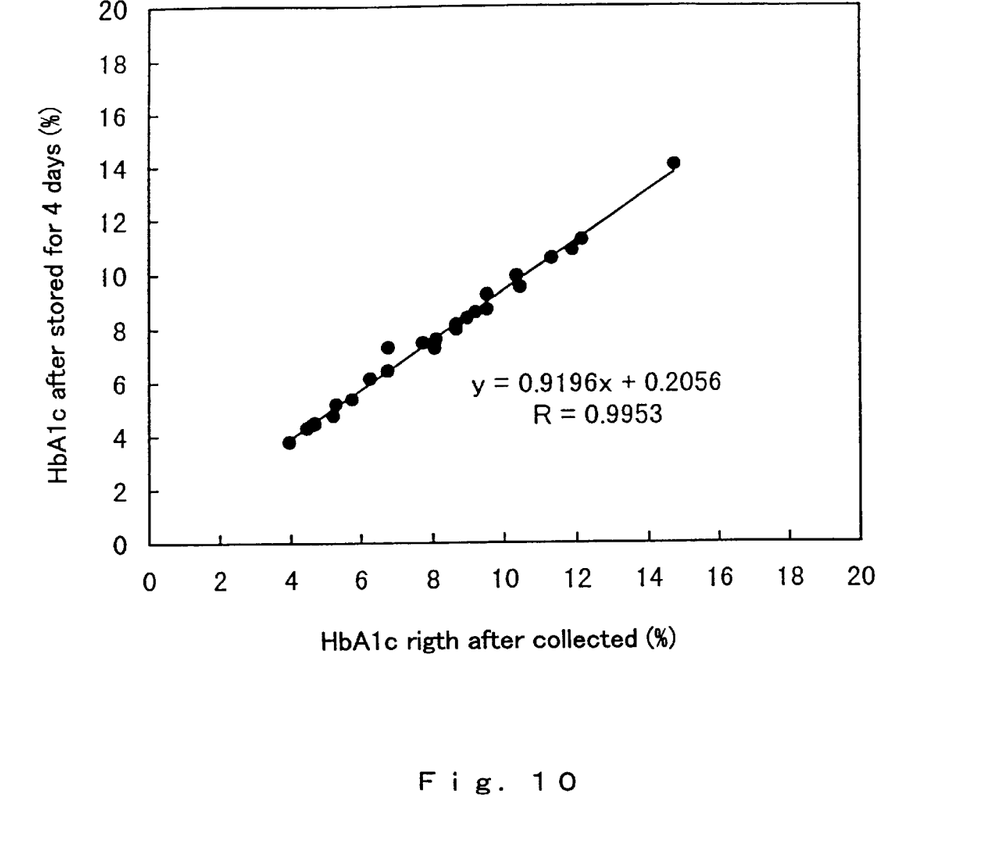
FIG. 10 is a graph showing the correlation between HbA1c stored for four days after the blood sample is collected by using a blood collection tube and HbA1c right after the blood sample is collected by using a blood collection tube in the above-mentioned embodiment according to the present invention.

Each test tool was impregnated with twenty-six blood samples collected by using EDTA, heparin and NaF respectively, and air-dried and stored for 1, 4, and 5 days. The part of the blood test tool f impregnated with the blood was punched out into a circle shape with a diameter of about 6 mm. Thus, the punched-out part was put into 0.6 ml of the eluate and allowed to stand still for about 10 minutes and the eluting procedure was performed. The HbA1c in the eluate was measured by using an automatic glycohemoglobin measuring device. Furthermore, HbA1c in blood sample right after collection was measured by using the automatic glycohemoglobin device measurement device. Then, the correlation between the amount of HbA1c in blood stored by the use of the blood test tool f and the amount of HbA1c in blood right after collection was examined. FIG. 9 is a graph showing the correlation between HbA1c in blood after stored for one day and HbA1c in blood right after collection; FIG. 10 is a graph showing the correlation between HbA1c in blood after stored for four days and HbA1c in blood right after collection; and FIG. 11 is a graph showing the correlation between HbA1c in blood after stored for five days and HbA1c right after collection.

Figure 11:
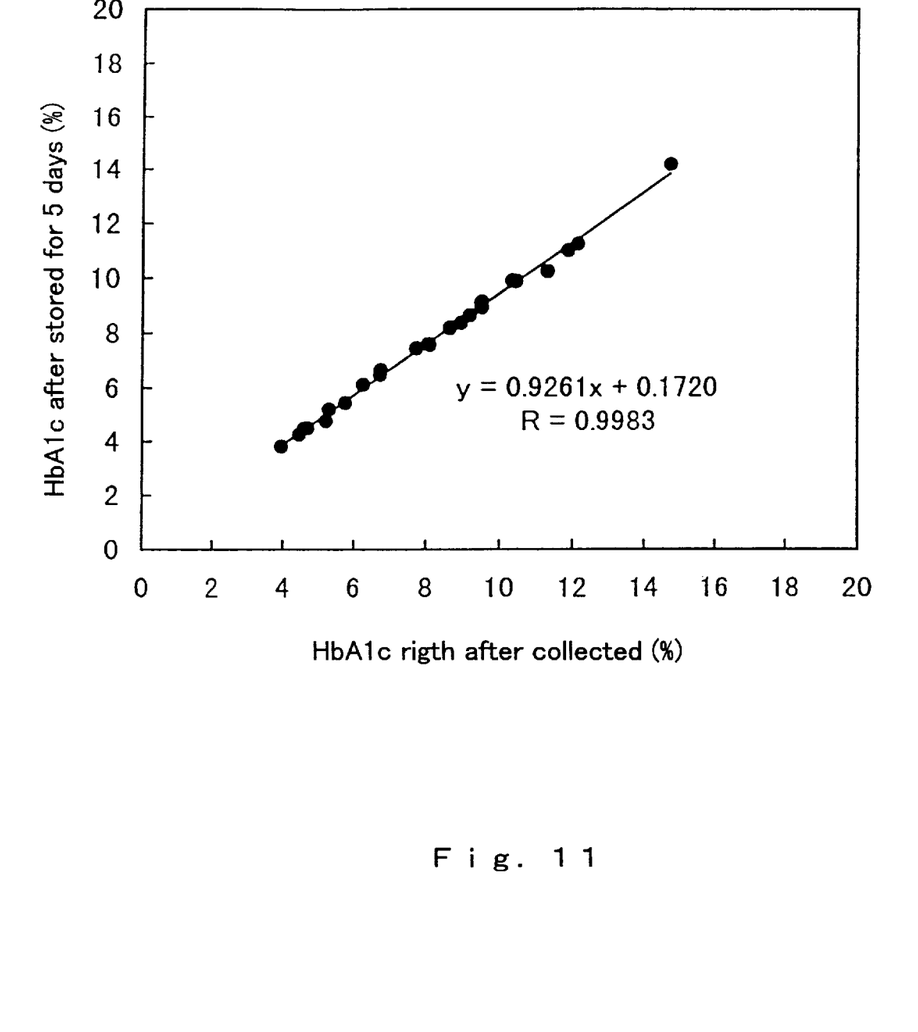
FIG. 11 is a graph showing the correlation between HbA1c stored for five days after the blood sample is collected by using a blood collection tube and HbA1c right after the blood sample is collected by using a blood collection tube in the above-mentioned embodiment according to the present invention.

As is apparent from graphs of FIGS. 9, 10 and 11, the amount of HbA1c when stored with the blood test tool f and the amount of HbA1c after collection shows a high correlation. Hereinafter, each formula of a regression line and correlation coefficient are shown.

(1) stored for one day formula of regression line Y=0.9667x+0.0979 correlation coefficient r=0.9987
(2) stored for four days formula of regression line Y=0.9196x+0.2056 correlation coefficient r=0.9953
(3) stored for five days formula of regression line Y=0.9261x+0.1720 correlation coefficient r=0.9983

EXAMPLE 7-4

Comparative Example 3

As shown in Table 4, monohydrate of citric acid and sucrose were dissolved in pure water so as to prepare six kinds of treatment solutions (i, j, k, l, m and n). Six blood test tools (i, j, k, l, m and n) were formed by impregnating the circular shaped filter paper with 2.5 ml of these treatment solutions. Moreover, remarks given to the blood test tools (i, j, k, l, m and n) correspond to the remarks of treatment solution (i, j, k, l, m and n). Furthermore, the blood test tools (l, m and n) were used in Comparative Example 3.

TABLE 4

| | Treated solution (mg/ml) | | | | | |
|---|---|---|---|---|---|---|
| | i | j | k | l | m | n |
| monohydrate of citric acid | 50 | 50 | 50 | 0 | 0 | 0 |
| sucrose | 0 | 100 | 300 | 0 | 100 | 300 |

Next, the blood test tool was impregnated with the blood collected in the presence of heparin from healthy subjects, and air-dried and stored for 0, 1, and 3 days at room temperature. Then, each part that was impregnated with the blood was cut out by a punch into a circle shape with a diameter of about 6 mm, and put into 0.6 ml of the eluate and allowed to stand still for about 10 minutes. HbA1c in this eluate was measured by the use of an automatic glycohemoglobin measuring device in a hemolytic mode. Furthermore, the protein-denaturation of Hb in each eluate was measured by the use of general purposed HPLC (La Chrom manufactured by Hitachi Ltd.). Moreover, as a control, fresh blood collected in the presence of heparin from healthy subjects was stored in a cold storage, and HbA1c was measured by the same manner after storage for 0, 1, and 3 days. Tables 5 and 6 show the results.

TABLE 5

| | Amount of HbA1c (%) | | |
|---|---|---|---|
| | Days stored | | |
| Blood test tool | 0 | 1 | 3 |
| i | 5.36 | 5.30 | 5.28 |
| j | 5.49 | 5.41 | 5.47 |
| k | 5.61 | 5.53 | 5.61 |
| l | 6.60 | 7.27 | 7.89 |
| m | 6.64 | 7.19 | 8.15 |
| n | 6.84 | 7.11 | 7.95 |
| Control | 5.91 | 5.90 | 5.87 |

TABLE 6

| | Amount of protein-denaturation Hb (%) | | |
|---|---|---|---|
| | Days stored | | |
| Blood test tool | 0 | 1 | 3 |
| i | 4.851 | 5.026 | 7.058 |
| j | 3.236 | 4.395 | 6.371 |
| k | 3.414 | 4.188 | 5.887 |
| l | 6.869 | 9.395 | 17.123 |
| m | 4.568 | 7.600 | 9.432 |
| n | 3.703 | 4.824 | 6.695 |
| control | 3.143 | 3.149 | 3.068 |

As is apparent from Table 5, in the blood test tools (i, j, and k) in the Example according to the present invention, the production of HbA1c was prevented. On the contrary, in blood test tools (l, m, and n) where citric acid was not used, the production of HbA1c was greater than the case of using the blood test tools (i, j and k). Furthermore, as is apparent from Table 6, in the blood test tools (i, j and k) of the Example according to the present invention, the protein-denaturation of Hb was prevented, particularly significantly in the blood test tools (j and k) where sucrose was used. On the other hand, in the blood test tool (l, m and n) wherein citric acid was not used, it was confirmed that the protein-denaturation of Hb tended to be prevented as the amount of sucrose was increased, however, the amount of the protein-denaturation of Hb was greater than the case where the blood test tools (i, j and k) were used.

Industrial Applicability

According to the method for preventing the denaturation of blood and the blood test tool of the present invention, it is possible to prevent the production of HbA1c and the protein-denaturation of Hb in a dried state blood. Therefore, when, for example, the blood test tool of the present invention is applied for clinical medicine, it is possible to determine HbA1c, which is an important index for diagnosis of diabetes, exactly and effectively.

What is claimed is:

1. A method for preventing the denaturation of blood in a dried state, wherein the blood in a dried state and carboxylic acid are allowed to be present together.

2. The method as defined in claim 1, wherein carboxylic acid is added to the blood in a non-dry state and then the blood is dried.

3. The method as defined in claim 1, wherein the carboxylic acid is at least one carboxylic acid selected from the group consisting of citric acid, oxalic acid, pyruvic acid and acetic acid.

4. The method as defined in claim 3, wherein the carboxylic acid is citric acid.

5. The method as defined in claim 2, wherein 1.5 to 10 parts by weight of carboxylic acid is added to 100 parts by weight of blood in a non-dry state.

6. The method as defined in claim 1, wherein a non-reducing sugar also is allowed to be present.

7. The method as defined in claim 6, wherein the non-reducing sugar is sucrose.

8. The method as defined in claim 1, wherein at least one of an anticoagulant and an antioxidant is allowed to be present.

9. The method as defined in claim 8, wherein the anticoagulant is at least one material selected from the group consisting of ethylenediaminetetraacetic acid, heparin and oxalic acid salt.

10. The method as defined in claim 8, wherein the antioxidant is any one of materials of glutathione and α-tocopherol.

11. The method as defined in claim 1, wherein the blood is in a dried state with a porous material impregnated with the blood and the blood dried.

12. A blood test tool which holds blood in a dried state with porous material impregnated with the blood, wherein a part of the porous material for holding blood contains carboxylic acid.

13. The blood test tool as defined in claim 12, wherein carboxylic acid is at least one carboxylic acid selected from the group consisting of citric acid, oxalic acid, pyruvic acid and acetic acid.

14. The blood test tool as defined in claim 13, wherein the carboxylic acid is citric acid.

15. The blood test tool as defined in claim 12, wherein the part for holding blood of the porous material contains also a non-reducing sugar.

16. The blood test tool as defined in claim 15, wherein the non-reducing sugar is sucrose.

17. The blood test tool as defined in claim 12, wherein the part for holding blood of the porous material is surrounded by a blood anti-diffusion layer provided in or around the porous material.

18. The blood test tool as defined in claim 17, wherein the blood anti-diffusion layer is a layer having a non-porous structure.

19. The blood test tool as defined in claim 17, wherein the blood anti-diffusion layer is hydrophobic.

20. The blood test tool as defined in claim 12, wherein the part for holding blood of the porous material is supported by a supporter and is detachable from the supporter.

21. The blood test tool as defined in claim 12, wherein the shape is cylindrical shape with a bottom and the bottom part is formed of a porous material.

* * * * *